United States Patent
Flanigan et al.

(10) Patent No.: US 6,893,655 B2
(45) Date of Patent: May 17, 2005

(54) TRANSDERMAL DELIVERY DEVICES

(75) Inventors: Peggy-Jean P. Flanigan, Woodbury, MN (US); Hye-ok Choi, Woodbury, MN (US)

(73) Assignee: 3M Innovative Properties Co., St. Paul, MN (US)

( * ) Notice: Subject to any disclaimer, the term of this patent is extended or adjusted under 35 U.S.C. 154(b) by 20 days.

(21) Appl. No.: 10/263,413

(22) Filed: Oct. 2, 2002

(65) Prior Publication Data
US 2003/0072792 A1 Apr. 17, 2003

Related U.S. Application Data
(60) Provisional application No. 60/328,333, filed on Oct. 9, 2001.

(51) Int. Cl.[7] .......................... A61F 13/02; A61F 13/00; A61L 15/16
(52) U.S. Cl. ....................... 424/448; 424/449; 424/443
(58) Field of Search .................. 424/448, 449, 424/443

(56) References Cited

U.S. PATENT DOCUMENTS

| | | |
|---|---|---|
| RE24,906 E | 12/1960 | Ulrich |
| 3,239,478 A | 3/1966 | Harlan, Jr. |
| 3,935,338 A | 1/1976 | Robertson |
| 4,181,752 A | 1/1980 | Martens et al. |
| 4,689,338 A | 8/1987 | Gerster |
| 4,693,776 A | 9/1987 | Krampe et al. |
| 4,732,808 A | 3/1988 | Krampe et al. |
| 4,952,650 A | 8/1990 | Young et al. |
| 5,169,727 A | 12/1992 | Boardman |
| 5,585,111 A | 12/1996 | Peterson |
| 5,637,646 A | 6/1997 | Ellis |
| 5,650,215 A | 7/1997 | Mazurek et al. |
| 5,753,768 A | 5/1998 | Ellis |
| 5,851,549 A * | 12/1998 | Svec .......................... 424/448 |
| 5,871,607 A * | 2/1999 | Hamilton et al. ........... 156/221 |
| 5,897,930 A | 4/1999 | Calhoun et al. |
| 5,986,011 A | 11/1999 | Ellis |
| 6,123,890 A | 9/2000 | Mazurek et al. |
| 6,143,317 A | 11/2000 | Himmelsbach et al. |
| 6,183,770 B1 * | 2/2001 | Muchin et al. ............. 424/448 |
| 6,197,397 B1 | 3/2001 | Sher et al. |
| 6,207,181 B1 | 3/2001 | Herrmann |

FOREIGN PATENT DOCUMENTS

WO     WO 96/08229     3/1996

OTHER PUBLICATIONS

Satas, *Handbook of Pressure Sensitive Adhesive Technology*, Second Edition, 1989, Van Nostrand Reinhold, New York (Table of Contents only).

* cited by examiner

*Primary Examiner*—Thurman K. Page
*Assistant Examiner*—Isis Ghali

(57) ABSTRACT

A transdermal delivery device including at least one pressure sensitive adhesive layer having a first major surface and a second major surface, wherein at least one of the first and second major surfaces is a structured surface; a cap layer in contact with the structured surface of an adhesive layer; and, at least one medicinal ingredient between the adhesive layer and the cap layer.

18 Claims, 6 Drawing Sheets

TRANSDERMAL DELIVERY DEVICES

RELATED APPLICATIONS

This application claims priority to U.S. Provisional Application No. 60/328,333 filed on Oct. 9, 2001.

TECHNICAL FIELD

The present invention relates to transdermal delivery devices including one or more pressure sensitive adhesive layers.

BACKGROUND

Transdermal drug delivery devices are well known in the pharmaceutical arts as a method for delivering a wide variety of drugs, such as nitroglycerin, estradiol, testosterone, fentanyl, and clonidine. Transdermal drug delivery devices typically involve a carrier (such as a liquid, gel, or solid matrix, or a pressure sensitive adhesive) into which the drug to be delivered is incorporated. Because the skin presents a substantial barrier to ingress of foreign substances into the body, it is often desirable or necessary to incorporate excipients into the carrier that enhance the rate at which the drug passes through the skin. Devices known to the art include reservoir type devices involving membranes that control the rate of drug and/or skin penetration enhancer delivery to the skin, single layer devices involving a dispersion or solution of drug and excipients in a pressure sensitive adhesive matrix, and more complex multilaminate devices involving several distinct layers, e.g., layers for containing drug, for containing skin penetration enhancer, for controlling the rate of release of the drug and/or skin penetration enhancer, and for attaching the device to the skin.

Typical reservoir devices contain a drug in a fluid carrier in the reservoir. The drug diffuses across a membrane to provide controlled release. Among the disadvantages of reservoir type devices are: the complexity of construction and manufacture; large size of the patch (area and thickness); lack of patient comfort; and unattractiveness.

Single layer devices where the drug is directly dispersed or dissolved in the adhesive layer overcome many of the disadvantages associated with reservoir devices. A major disadvantage of single layer devices, however, is the loss of thermodynamic driving force for the drug as the device becomes depleted of drug during the wear period. This loss of driving force causes a decrease in drug delivery rate and often results in a large excess of drug remaining in the device, which is discarded at the end of the wear period.

SUMMARY

U.S. Pat. No. 6,197,397 B1 (Sher et al.), U.S. Pat. No. 5,897,930 (Calhoun et al.) and U.S. Pat. Nos. 5,650,215 and 6,123,890 (Mazurek et al.) describe articles having adhesive layers with a precisely replicated surface topography. The performance properties of the articles can be tailored by independently varying the rheological properties of the adhesive and the structures formed in the adhesive layer. For example, channels in the adhesive layer may be used to provide fluid egress when the article is adhered to a substrate, while pegs and posts may be used to control the level of adhesion to the substrate.

If an overlayer is placed in contact with a surface of a structured layer having a surface topography, certain regions of the structured layer become discrete or discontinuous channels or reservoirs that may be used to advantage to tailor the properties of the laminate construction. For example, if a cap layer is placed in contact with and overlies a structured surface of an adhesive layer, the regions between the structures in the adhesive matrix, or the structures themselves, form an array of partially or fully enclosed reservoirs. Copending U.S. Ser. No. 09/974,710, incorporated herein by reference, describes how this array of reservoirs may be used, alone or in combination with unstructured adhesive layers or additional structured adhesive layers, to provide laminate articles with a wide range of unique properties.

In one aspect, the present invention resides in the finding that the precisely replicated topography of the structured layers provides a precisely defined void volume that is useful in a transdermal drug delivery device. The ability to provide a defined void volume within a transdermal drug delivery device has a number of benefits and uses. Among these is the ability to contain a medicinal ingredient within the void volume, which can temporally alter the thermodynamic driving force in the skin contacting layer by replenishing the skin contacting layer with drug, penetration enhancers, or other excipients. The construction of the present invention permits the drug to continuously replenish the skin contact layer as the drug is depleted during the wear period with a minimum of deformation of the device. The transdermal delivery devices of the present invention retain their initial appearance over the course of the wear period. This is an improvement over traditional single reservoir devices that become wrinkled and disfigured over the course of the wear period as the reservoir becomes depleted over time.

A controllably contained medicinal ingredient also may be segregated from the skin contacting layer, such that the liquid is not released during the intended use of the device, but will be released upon misusing the device. The presence of a plurality of microscopic reservoirs also minimizes the amount of unused drug that remains in the device when it is discarded at the end of the wear period.

In one aspect, the invention is a transdermal delivery device including at least one pressure sensitive adhesive layer having a first major surface and a second major surface, wherein at least one of the first and second major surfaces is a structured surface; a cap layer in contact with the structured surface of an adhesive layer; and, at least one medicinal ingredient between the adhesive layer and the cap layer.

In a second aspect, the invention is a method of administering a drug, including: (a) providing a transdermal delivery device including: at least one pressure sensitive adhesive layer having a first major surface and a second major surface, wherein at least one of the first and second major surfaces is a structured surface, and a cap layer in contact with a structured surface of the adhesive layer, and at least one medicinal ingredient between the adhesive layer and the cap layer; b) placing the transdermal delivery device upon a patient's skin at an administration site; and c) maintaining contact with the skin for a time to deliver a therapeutically effective amount of the medicinal ingredient.

In a third aspect, the invention is a transdermal delivery device, including: (a) first adhesive layer having a first major surface and a second major surface, wherein at least one of the first and second major surfaces is a structured surface, wherein the first adhesive layer comprises at least one first array of reservoirs, and wherein the first array of reservoirs is at least partially filled with one of air and a first medicinal ingredient; and (b) a second adhesive layer having a first major surface and a second major surface, wherein at least one of the first and second major surfaces is a structured surface, wherein the second adhesive layer comprises at least one second array of reservoirs, and wherein the second array of reservoirs is at least partially filled with a second medicinal ingredient.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
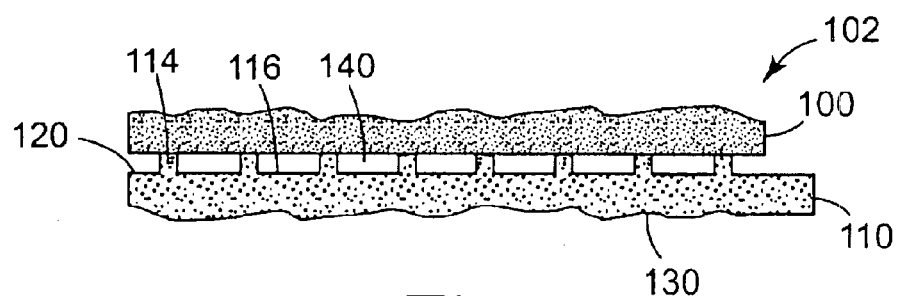
FIG. 1 is a cross-sectional view of a transdermal delivery device.

In one aspect, the invention is a transdermal delivery device having a plurality of reservoirs for encapsulating medicinal ingredients within the layers of a laminate construction. Referring to FIG. 1, a transdermal delivery device is shown that includes at least one structured layer 110 and a cap layer 100. Preferably, the structured layer 110 is a layer of a pressure sensitive adhesive, and the cap layer is a backing. Alternatively, the structured layer is a polymeric film and the cap layer is an unstructured layer of an adhesive.

Any pressure sensitive adhesive, including those described in Satas, et al., *Handbook of Pressure Sensitive Adhesives,* 2d ed. 1989, is suitable for the pressure sensitive adhesive layers of the present invention. Useful pressure sensitive adhesives for the purposes of the present invention include those which are capable of retaining a structured surface after being embossed with a structured molding tool and after being subsequently removed from the structured molding tool.

Classes of suitable pressure sensitive adhesives include, for example, acrylics, natural and synthetic rubbers, ethylene vinyl acetate, poly(alpha-olefins), vinyl ethers, and silicones. The adhesives may be in the form of copolymers, bicontinuous adhesives, hydrogels, latex emulsions, macromers, and block copolymers. Suitable block copolymers are commercially available from Shell Oil Company (Houston, Tex.) under the trade designation KRATON.

More preferred pressure sensitive adhesives include, for example, acrylics, poly(olefins), KRATON, and silicones, and acrylics are particularly preferred. Suitable acrylic adhesives are disclosed, for example, in U.S. Pat. Nos. 3,239,478, 3,935,338, 5,169,727, RE 24,906, 4,952,650, 4,181,752, 5,986,011, 5,637,646 and 5,753,768. A suitable class of acrylate pressure sensitive adhesives is the reaction product of at least one alkyl acrylate with at least one reinforcing comonomer. Suitable alkyl acrylates are those having a homopolymer glass transition temperature below about −10° C. and include, for example, n-butyl acrylate, 2-ethylhexylacrylate, isoctylacrylate, isononyl acrylate, ethylene monoacrylate, octadecyl acrylate and the like. Suitable reinforcing monomers include, for example, acrylic acid, itaconic acid, isobornyl acrylate, N,N-dimethylacrylamide, N-vinyl caprolactam, N-vinyl pyrrolidone, and the like.

The pressure sensitive adhesives can be prepared and coated using a variety of standard methods. For example, the pressure sensitive adhesives can be polymers that are dispersed in solvent or water and coated onto a liner or molding tool. If a solvent borne or water borne pressure sensitive adhesive composition is employed, then the adhesive layer may undergo a drying step to remove all or a majority of the carrier liquid. The adhesive may be cured using an energy source (e.g., heat, UV radiation, e-beam, and the like). Alternatively, adhesives may be applied without dispersal in a solvent or water using a variety of methods, such as, for example, melting or extruding the adhesive onto a liner or molding tool. The adhesive can be cross-linked with an energy source such as heat, UV radiation, e-beam radiation, and the like. In yet another alternative, monomeric pre-adhesive compositions can be coated onto a liner or molding tool and polymerized and cross-linked with an energy source, as described above.

The surface of the liner or molding tool may have applied thereon regions of different adhesives, such as for example, alternating strips of two different adhesive formulations, or may include multiple layers, each with different adhesive formulations.

The thickness of the adhesive layer 100 may vary widely depending on the intended application, and typically ranges from about 2 $\mu$m to about 800 $\mu$m, preferably from about 20 $\mu$m to about 150 $\mu$m.

The adhesive can optionally include one or more additives such as, for example, initiators, fillers, plasticizers, cross-linkers, tackifiers, chain transfer agents, fibrous reinforcing agents, woven and non-woven fabrics, foaming agents, antioxidants, stabilizers, fire retardants, viscosity enhancing agents, coloring agents, and mixtures thereof.

Referring again to FIG. 1, at least one major surface 120 of the adhesive layer 110 in the article 102 includes a structured topography. The structured topography includes structures 114 with specific shapes that form a plurality of discrete reservoirs or channels 140 when overlain by the cap layer 100. Preferably, the structures form a substantially regular array or pattern in the adhesive layer and include, for example, rectilinear patterns, polar patterns, geometric patterns, and cross-hatch patterns. The array or pattern of structures may optionally reside on both major surfaces 120, 130 of the adhesive layer 110 (not shown in FIG. 1). The shape, size and distribution of the structures 114 in the adhesive layer 110 may be precisely controlled to provide an array of reservoirs or channels 140 with a particular size, while maintaining a known contact area between the cap layer 100 and the adhesive layer 110.

The design and position of the structures (i.e., pitch, depth, size, contact area, wall and post width, and shape) can be controlled to achieve precise placement of reservoirs of specific sizes and shapes. The constructions of the invention can include a high density and highly regulated placement of the reservoirs or channels 140, which can be tailored according to the needs of a particular application.

The reservoirs of the structured adhesive layer are at least partially filled with air and/or at least one type of medicinal ingredient intended to have a medicinal or therapeutic effect. Optionally, the adhesive matrix of one or more of the adhesive layers can include medicinal ingredients, either the same as or different than the substances present in the reservoirs. Medicianl ingredients can be incorporated into the adhesive composition prior to or after curing of the adhesive layer(s).

The medicinal ingredient can be a drug, antimicrobial agent, antifungal agent, cosmetic agent, or pharmaceutically effective excipient. In a preferred embodiment, the medicinal ingredient is a drug. As used herein, the term "drug," includes its equivalents, "bioactive agent," and "medicament" and is intended to have the broadest meaning as including substances intended for use in the diagnosis, cure, mitigation, treatment or prevention of disease, or to affect the structure or function of the body. The drug, or an acceptable salt thereof, will be present in an amount such that the composition delivers a therapeutically effective amount for the indication being treated. The amount that constitutes a therapeutically effective amount will vary according to the type of drug used, the condition to be treated, any drugs being coadministered with the selected drug, the amount of time the composition is allowed to remain in contact with the skin of the subject, and other factors known to those of skill in the art. However, the amount of drug present in the transdermal drug delivery composition of the invention will generally be about 0.01 to 40 wt. %, preferably about 1.0 to 20 wt. %, based on the total weight of the composition.

Any drug that is suitable for transdermal delivery can be used in the transdermal drug delivery composition of the invention. Examples of useful drugs include, but are not limited to, anti-inflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotozoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., zileuton), and angiotensin converting enzyme inhibitors (e.g., captopril, lisinopril); other antihypertensives (e.g., propranolol); leukotriene antagonists; anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); sex hormones (e.g., estrogens, testosterone, progestins such as levonorgestrel, norethindrone, gestodene); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatriptan); antiarrhythmic agents (e.g., flecainide); antiemetics (e.g., metaclopromide, ondansetron); anticancer agents (e.g., methotrexate); neurologic agents such as anxiolytic drugs; hemostatics; antiobesity agents; and the like, as well as pharmaceutically acceptable salts and esters thereof. Preferred drugs include morphine and fentanyl.

Other preferred medicinal ingredients are certain pharmaceutically or medically effective excipients. These excipients may include softening agents (softeners), skin penetration enhancers or solubilizers in transdermal drug delivery systems. Exemplary materials include $C_8$–$C_{36}$ fatty acids such as isostearic acid, octanoic acid, and oleic acid; C8–$C_{36}$ fatty alcohols such as oleyl alcohol and lauryl alcohol; lower alkyl esters of $C_8$–$C_{36}$ fatty acids such as ethyl oleate, isopropyl myristate, butyl stearate, and methyl laurate; di(lower) alkyl esters of $C_6$–$C_8$ diacids such as diisopropyl adipate; monoglycerides of $C_8$–$C_{36}$ fatty acids such as glyceryl monolaurate; tetraglycol (tetrahydrofurfuryl alcohol polyethylene glycol ether); tetraethylene glycol (ethanol, 2,2'-(oxybis(ethylenoxy))diglycol); $C_6$–$C_{36}$ alkyl pyrrolidone carboxylates; polyethylene glycol; propylene glycol; 2-(2-ethoxyethoxy)ethanol; diethylene glycol monomethyl ether; N,N-dimethyldodecylamine-N-oxide and combinations of the foregoing. Alkylaryl ethers of polyethylene oxide, polyethylene oxide monomethyl ethers, and polyethylene oxide dimethyl ethers are also suitable, as are solubilizers such as glycerol and N-methyl pyrrolidone. The terpenes are another useful class of additives, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Of the terpenes, terpineol, particularly α-terpineol, is preferred.

Preferred excipients include glyceryl monolaurate, terpineol, lauryl alcohol, tetraglycol, tetraethylene glycol, propylene glycol, isopropyl myristate, ethyl oleate, methyl laurate, and 2-(2-ethoxyethoxy)ethanol.

The excipients (s) can be dispersed, preferably substantially uniformly, and more preferably dissolved in the adhesive. Where the excipient is a penetration enhancer, it is present in an amount that enhances drug permeation through the skin compared to a like composition not containing the penetration enhancer(s) when this phenomenon is measured using an in vitro skin penetration test method, as described in U.S. Pat. No. 5,585,111. Other additives present may include anti-oxidants, colorants, and the like. The total amount of additive will generally be about 5 to about 40% by weight based on the total weight of the composition.

Medicinal ingredients can be in a variety of forms, such as, for example, solids, liquids, gels, pastes, foams, powders, agglomerated particles, crystals, microspheres, microcapsules, microencapsulated liquids, suspensions, and the like.

The reservoirs or channels 140 are at least partially covered by a cap layer 100 (described below) that encapsulates the medicinal ingredients within the void volume of the reservoirs or channels. This plurality of discrete, encapsulated reservoirs compartmentalizes the encapsulated substances and minimizes communication between the contents of neighboring reservoirs within the same or different adhesive layers. In contrast, channels are substantially continuous voids that provide unrestricted or less restricted movement of the substances within the adhesive layer.

One or more additional structured and substantially non-structured adhesive and/or non-adhesive layers can be laminated to the second major surface 130 or the cap layer 100 on the side opposite the second major surface 130. Each layer can be structured on one or both sides and can include one or more types of structures and adhesive and non-adhesive materials.

The structured adhesive layer(s) of the device can include controlled amounts of one or more medicinal ingredients. The benefit of having a controlled amount of material contained in each layer of the device is the ability to precisely load a desired amount of material into the device without compromising the favorable thermodynamic driving force that characterizes a single reservoir device. The construction permits the medicinal ingredient to continuously replenish the skin contact layer as the drug is depleted during the wear period with a minimum of deformation of the device. This plurality of discrete, encapsulated reservoirs can be advantageous for compartmentalizing the encapsulated medicinal ingredients and minimizing communication between the contents of neighboring reservoirs within the same or different adhesive layers. In a device with a large, macroscopic reservoir, the contents of the reservoir may not always be evenly dispersed within the reservoir, since fluid may accumulate in different portions of the reservoir due to outside forces of gravity or pressure. This uneven accumulation can alter the controlled release characteristics of a reservoir device. A benefit of multiple reservoirs is the ability to more evenly control the dispersal of drug within the device, even after the device has become depleted of a portion of its contents. Segregation of the different medicinal ingredients within different layers of the construction can also provide controlled release of one or more of the medicinal ingredients temporally.

The shapes of the structures in the adhesive layer may be varied depending on the application. The structures and constructions can be altered depending on the total volume of medicinal ingredients, the rate of delivery, and the peel adhesion required for a particular application. The height and width of the structures 114, which may extend above and/or below the plane of the adhesive layer, may be selected to achieve the desired performance. Suitable discrete shapes for the structures 114 include hemispheres, right pyramids, trigonal pyramids, prisms (such as square prisms, rectangular prisms, cylindrical prisms and other similar polygonal features), square pyramids, quadrangle pyramids, circles, ellipsoids and polygons (e.g., hexagons and diamonds). Suitable substantially continuous and interconnecting shapes for the structures include grooves (e.g., "V" grooves) and ridges (e.g., "Y" shaped ridges). The final dimensions of the structures may vary widely depending on the rheology of the adhesive layer and the application conditions. Although the structures within the adhesive are designed to be of substantially regular shape, irregularities may arise because the adhesive may partially creep over time.

Combinations of the different structure shapes, sizes, and orientations can be utilized in different regions of the adhesive layer 110, or a particular region of the adhesive layer 110 may include patterns with multiple or overlapping structures.

Figure 2:
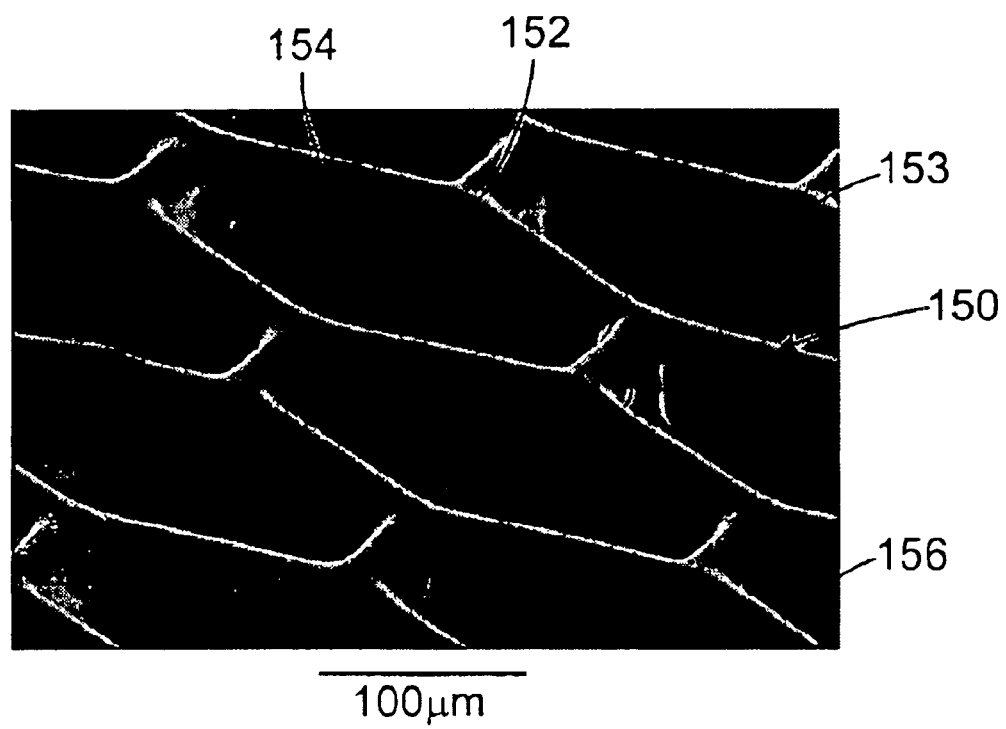
FIG. 2 is a scanning electron micrograph of a close-packed hexagonal structured adhesive.

To provide a substantially large reservoir void volume for a particular area of an adhesive layer, preferred structures include hexagons and diamonds. One suitable structure for this purpose is shown in FIG. 2, which includes hexagonal structures 150, each forming a reservoir 152 in the adhesive layer 153. Each reservoir 152 is enclosed by six sidewalls or posts 154, which protrude above the surface of the adhesive layer 156.

Figure 3:
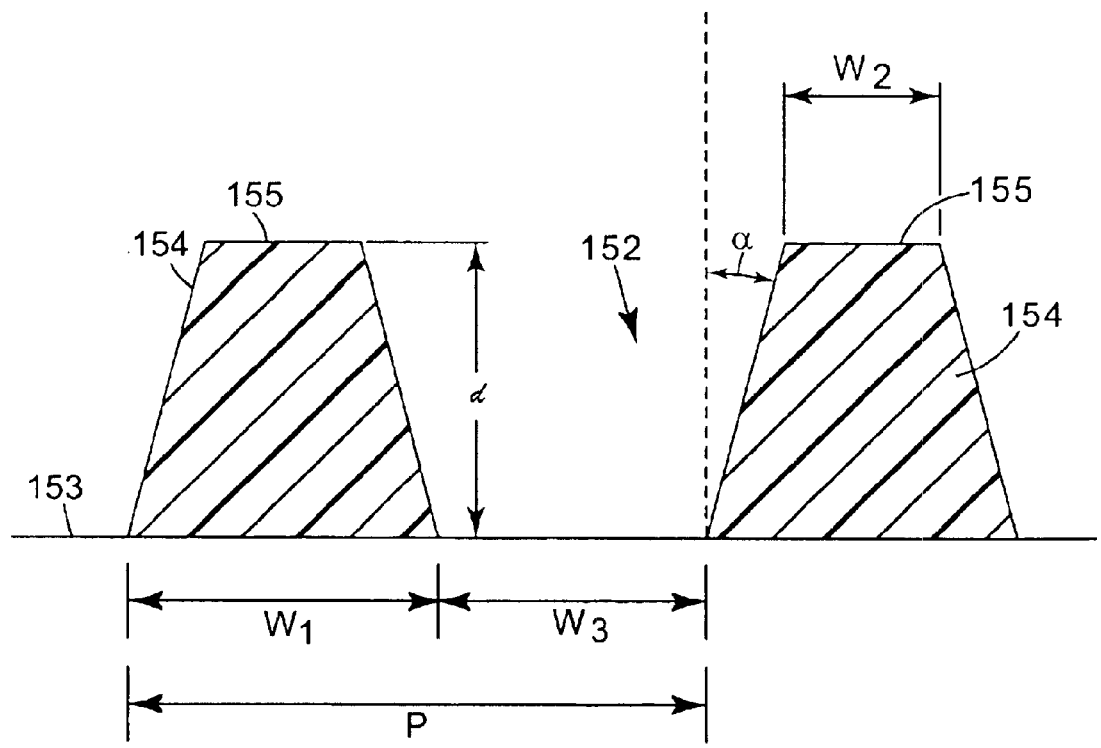
FIG. 3 is a cross-sectional view of the structured adhesive layer of FIG. 2.
Figure 4:
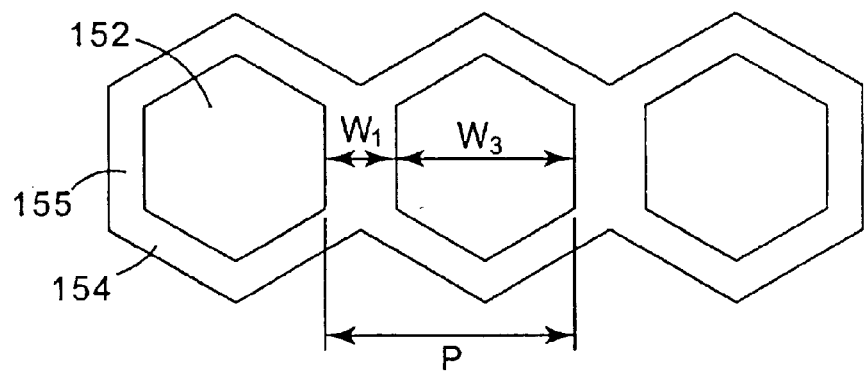
FIG. 4 shows the pitch dimension of the structured adhesive layer of FIG. 2.

FIG. 3 shows two substantially parallel sidewalls 154 of a hexagonal structure 150 of FIG. 2. Referring to FIG. 3, the sidewalls 154 each make an angle α with respect to a plane normal to the surface 156 of the adhesive layer 153. The angle α may be selected from an angle greater or equal to 0° and less than 90°, measured with respect to the plane of the surface of adhesive layer 156. The angle α is preferably greater than about 0° and less than about 45°, more preferably greater than about 2° and less than about 20°. The depth of each reservoir or channel 152, measured from a plane of the adhesive layer 156 to the top 155 of the sidewall 154 is preferably less than 2 mm; more preferably about 10 µm to about 200 µm; most preferably about 70 µm to about 150 µm. The width of the sidewall 154 at its base $W_1$ is preferably between about 5 µm and about 5 mm, more preferably between about 20 µm and about 80 µm. The distance $W_2$ across the top 155 of the sidewall 154 is preferably less than 2 mm, more preferably about 0.05 µm to about 60 µm. The distance $W_3$ between the bases of the sidewalls 154 is preferably less than about 30 mm, more preferably less than about 5 mm, most preferably about 50 µm to about 250 µm, as measured between any two parallel sidewalls 154 of the reservoir or channel 152 (see also FIG. 4). The sum of $W_1$ and $W_3$ defines the repeat unit of the pattern and is referred to herein as the pitch.

In the case of discrete reservoirs 152, each discrete reservoir has a void volume of less than about 100 µl; preferably less than 20 nL; more preferably less than 4 nL. The number of reservoirs 152 per unit area of the adhesive layer 156 is generally between about 5 E+06/cm$^2$ to 1/cm$^2$; preferably about 1.20 E+03 to about 1.00 E+06/cm$^2$. Preferably, the pattern of structures defines a discrete void volume of above 20 nL to about 80 µL more preferably between about 20 nL to about 20,000 nL on any 1 cm$^2$ area of the adhesive layer 156.

Discontinuous reservoirs or channels generally have a void volume between 0.1 and 99.9% of the total volume of the adhesive layer, preferably 0.5 to 50%, and more preferably 1 to 20%.

Referring again to FIG. 1, the cap layer 100, which is preferably a substantially continuous layer, can be, for example, a structured or non-structured backing, a structured or non-structured adhesive layer, a membrane, or the like. The contact area between the structures 114 on the first major surface 120 and the cap layer 100 may vary widely depending on the intended application, and is between about 0.5% and about 99%; preferably between about 5% to about 80%; and more preferably between about 20% to about 40%. For example, for a close-packed hexagonal structure (FIG. 2), $$\text{the theoretical percent contact area equals} = \left[1 - \frac{(p-w)^2}{p^2}\right] * 100,$$

where p=pitch and w=width of wall at point of contact (also referred to above as $W_2$).

In one preferred embodiment of the invention, the cap layer 100 is a backing. As used herein, the term backing refers to a thin sheet, which, after being placed in intimate contact with the adhesive, cannot be subsequently removed without damaging adhesive coating. The backing protects the adhesive and any components contained in the adhesive layer and/or reservoirs or channels from the environment.

The backing can be occlusive, non-occlusive or a breathable film as desired. It is also often desirable to have a conformable backing since a stiff backing may cause mechanical irritation to the skin. In order to maintain the health of the covered skin during long term wear (e.g., for periods in excess of day), it may be desirable for the backing to have a relatively high permeability to oxygen. Further, as the backing is in contact with the pressure sensitive adhesive layer and the components contained in the pressure sensitive adhesive and/or reservoirs, including the drug and any excipients, it is important that the backing be stable and substantially non-reactive to such components in order that the backing retains its structural integrity and conformability. It is also important that the backing not absorb the drug or excipients from the pressure sensitive adhesive or the reservoirs. It may also be desirable for the backing to be heat sealable at a relatively low temperature to a variety of other polymeric substrates.

The backing preferably has sufficient structural integrity such that the backing is capable of being coated and/or handled. Backings can be made of any material conventionally utilized as a tape backing or may be made of other flexible or stiff material. Typical examples of flexible tape backing materials include those made of paper, plastic films such as polypropylene, polyethylene, particularly low density polyethylene, linear low density polyethylene, metallocene polyethylenes, high density polyethylene, polypropylene, polyvinyl chloride, polyester (e.g., polyethylene terephthalate), randomly oriented nylon fibers, ethylene-vinyl acetate copolymer, polyurethane, vinyl, polyvinylidene fluoride, cellulose acetate and ethyl cellulose, and polyamide films such as those commercially available from E.I. DuPont de Nemours & Co. (Wilmington, Del.) under the trade designation KAPTON.

Preferred backings include SCOTCHPAK 1109, SCOTCHPAK 9732 and COTRAN 9720, which are available from 3M Company (St. Paul, Minn.).

Backings also can be prepared of fabric such as woven fabric formed of threads of synthetic or natural materials such as cotton, nylon, rayon, glass, polyester, ceramic material, and the like, or nonwoven fabric such as air laid webs of natural or synthetic fibers or blends of these. The backing may also be formed of metal, metalized polymeric films, glass, wood, or ceramic sheet materials. Backings that are layered such as polyethylene terephthalate-aluminum-polyethylene composites are also suitable.

Backing materials can be pretreated (i.e., primed). Common pretreatments include corona treatment and chemical priming.

Figure 5A:
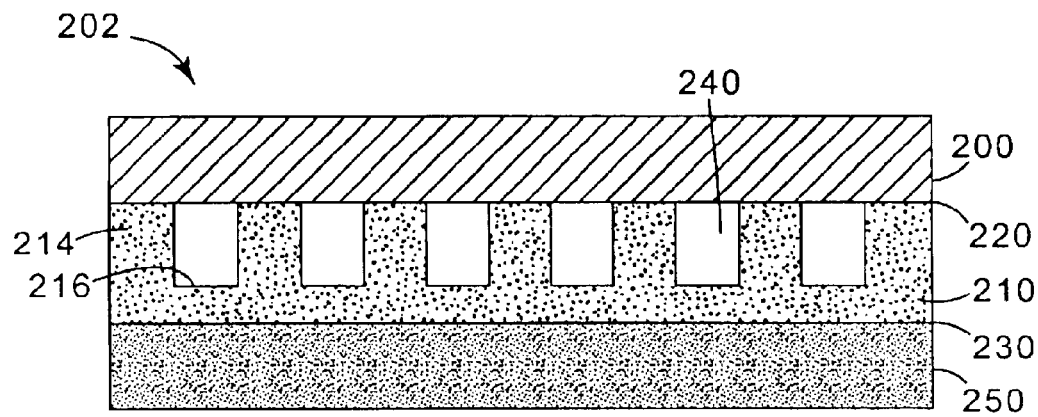
FIG. 5A is a cross-sectional view of a transdermal delivery device including a skin contact pressure sensitive adhesive layer.

Referring to FIG. 5A, a transdermal delivery device 202 is shown in which the cap layer 200 is a backing. The construction includes at least one adhesive layer 210 having at least one structured major surface 220. The first major surface 220 of the adhesive layer 210 includes structures 214 and land areas 216. The regions between the structures 214 in contact with the cap layer 200 creates a plurality of reservoirs 240. The construction 202 further includes a non-structured adhesive layer 250, which contacts the non-structured second major surface 230 of the adhesive layer 210.

Figure 5B:
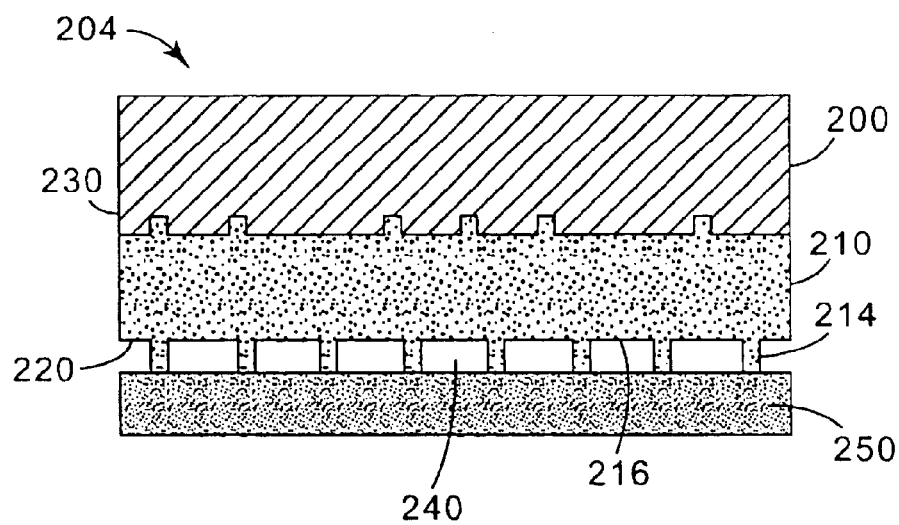
FIG. 5B is a cross-sectional view of the transdermal delivery device of FIG. 5A including a pressure sensitive adhesive layer with structures facing toward the skin contact pressure sensitive adhesive layer.

Alternatively, as shown in the construction 204 in FIG. 5B, the structured first major surface 220 of the adhesive layer 210 is in contact with a second pressure sensitive adhesive layer 250, and the second major surface 230 is in contact with the cap layer 200, which is preferably a backing.

The additional pressure sensitive adhesive layer 250 of this embodiment is particularly suitable for contact with a patient's skin and is referred to herein as the "skin contact pressure sensitive adhesive layer." Any pressure sensitive adhesive is suitable for the skin contact layer 250, and preferred compositions have good permeability to water vapor (e.g., perspiration) and air. The pressure sensitive adhesive can be either the same as or different than the pressure sensitive adhesive used in the structured adhesive layer 210. Suitable skin contact pressure sensitive adhesives include acrylate copolymers, synthetic rubbers such as polyisobutylenes, polyisoprenes, styrenic block copolymers, polyvinylethers, silicone polymers, and combinations thereof.

Acrylate copolymers are preferred pressure sensitive adhesives for use in the skin contact pressure sensitive adhesive layer. Suitable acrylate copolymers for use in an adhesive layer preferably comprise about 45 to about 95 percent by weight, more preferably 55 to 95 percent by weight, based on the total weight of all monomers in the copolymer, of one or more A monomers selected from the group consisting of alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. Preferred alkyl acrylates include isooctyl acrylate, 2-ethylhexyl acrylate, n-butyl acrylate, and cyclohexyl acrylate. Isooctyl acrylate is a particularly preferred A monomer.

The preferable acrylate copolymer further comprises about 5 to about 55 percent by weight, more preferably about 5 to about 40 percent by weight, based on the total weight of all monomers in the copolymer, of one or more B monomers. Suitable B monomers include those containing a functional group selected from the group consisting of carboxylic acid, sulfonamide, urea, carbamate, carboxamide, hydroxy, amino, oxy, oxo, and cyano. Exemplary B monomers include acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, N-vinyl-N-methyl acetamide, N-vinyl valerolactam, N-vinyl caprolactam, N-vinyl-2-pyrrolidone, glycidyl methacrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl acrylate, furfuryl methacrylate, tetrahydrofurfuryl acrylate, tetrahydrofurfuryl methacrylate, propylene glycol monomethacrylate, propylene oxide methyl ether acrylate, di(lower)alkylamino ethyl acrylate, di(lower)alkylamino ethyl methacrylate, di(lower alkyl)aminopropyl methacrylamide, acrylonitrile, and methacrylonitrile. Preferred B monomers include acrylic acid, methacrylic acid, acrylamide, methacrylamide, hydroxyethyl acrylate and vinyl acetate.

The copolymer may optionally further comprise a substantially linear macromonomer copolymerizable with the A and B monomers and having a weight average molecular weight in the range of about 500 to about 500,000, preferably about 2,000 to about 100,000 and more preferably about 5,000 to about 30,000. The macromonomer, when used, is generally present in an amount of not more than about 20%, preferably not more than about 10% by weight based on the total weight of all monomers in the copolymer. Suitable macromonomers include polymethylmethacrylate, styrene/acrylonitrile, polyether, and polystyrene macromonomers. Examples of useful macromonomers and their preparation are described in Krampe et al., U.S. Pat. No. 4,693,776, the disclosure of which is incorporated herein by reference.

The copolymers described above can be prepared by methods well known to those skilled in the art and described for example in U.S. Pat. No. RE 24,906 (Ulrich), U.S. Pat. No. 4,732,808 (Krampe et. al.), and International Publication Number WO 96/08229 (Garbe et. al.), the disclosures of which are incorporated herein by reference.

The construction can further include a membrane (not shown in FIG. 5B) interposed between the structured adhesive layer 210 and the skin contact pressure sensitive adhesive layer 250. Membranes serve a variety of purposes, such as controlling diffusion and providing controlled release of a drug. The membrane is selected such that it is rate controlling, i.e., the presence of the membrane in the device may change the skin penetration profile of the device compared to a like device not having the membrane. The membrane is preferably made of a flexible, polymeric material used conventionally by those skilled in the art. Suitable membranes include continuous film membranes and microporous membranes. Preferred membranes are continuous film membranes prepared from ethylene:vinyl acetate copolymers containing from about 0.5 to about 28 wt. % vinyl acetate. The membrane thickness can generally be from about 25 μm to about 100 μm, preferably the thickness can be from about 50 μm to about 75 μm.

Figure 6A:
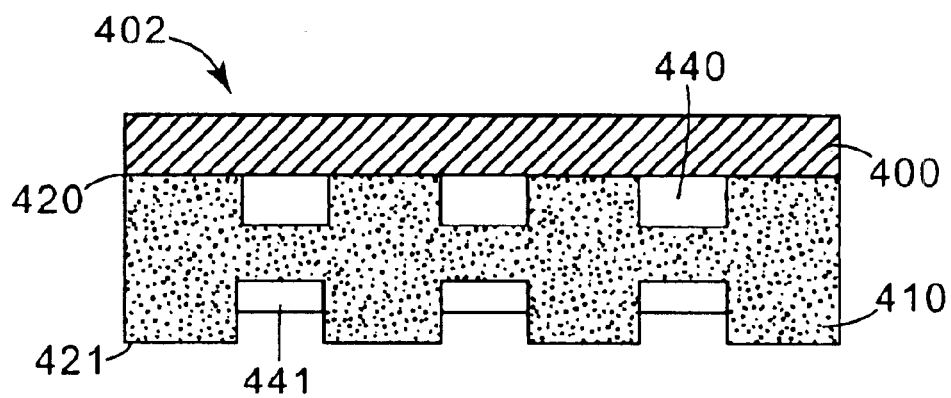
FIG. 6A is a cross-sectional view of a transdermal delivery device having one structured layer and an exposed structured surface.

In another aspect, the invention is a transdermal delivery device that includes at least one pressure sensitive adhesive layer having an exposed structured surface suitable for contact with a target substrate (e.g., a patient's skin) and a plurality of encapsulated microscopic reservoirs. In one embodiment, shown in FIG. 6A, the device 402 includes a pressure sensitive adhesive layer 410 having two structured major surfaces 420 and 421. The first major surface 420 is in contact with a cap layer 400. The construction includes a plurality of encapsulated microscopic reservoirs 440 that are covered by the cap layer 400. The second major surface 421 is an exposed, structured surface that includes a plurality of reservoirs 441. The first and second major surfaces 420 and 421, respectively, can have the same topography or a different topography. Optionally, one or more additional structured adhesive layers (not shown in FIG. 6A) can be interposed between the structured layer 410 and the cap layer 400. One or more types of medicinal ingredients can be loaded into the reservoirs 440 and 441 of the construction 402.

Figure 6B:
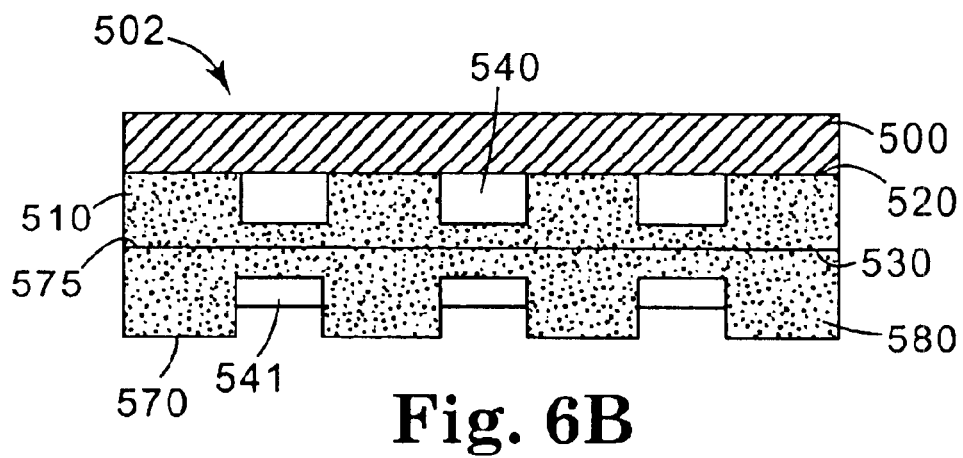
FIG. 6B is a cross-sectional view of a multi-layer transdermal delivery device having two structured layers and an exposed structured surface.

Referring to FIG. 6B, an article 502 is shown with an adhesive layer 510 including a non-structured first major surface 530 and a structured second major surface 520. The layer 510 includes a plurality of reservoirs 540. The article 502 includes a second adhesive layer 580 having a structured first major surface 570 and a substantially non-structured second major surface 575. The structured major surface 520 of the adhesive layer 510 contacts a cap layer 500 and encapsulates a plurality of reservoirs 540. Alternatively, the structured surface 570 can be contact with a skin contact pressure sensitive adhesive layer. The article 502 can further include one or more additional structured layers interposed between the structured layer 510 and the cap layer 500 (not shown in FIG. 6B).

Figure 6C:
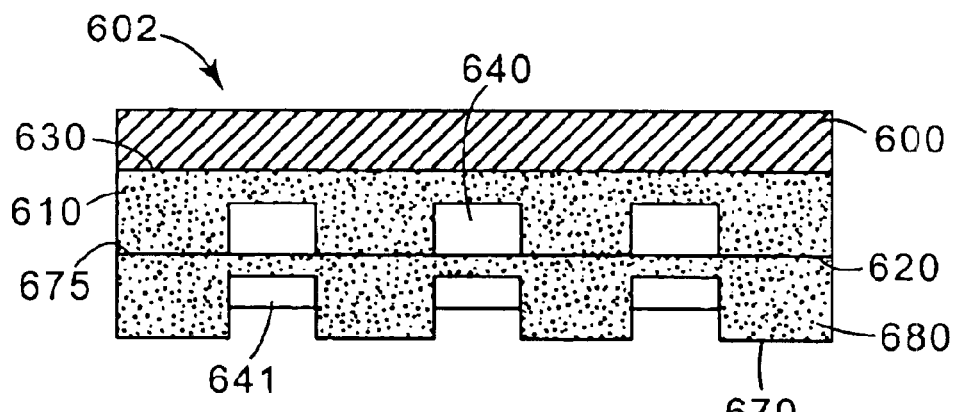
FIG. 6C is a cross-sectional view of the multi-layer transdermal delivery device of FIG. 6B having the structured surfaces facing away from the cap layer.

Referring to FIG. 6C, an article 602 is shown that includes an adhesive layer 610 with a non-structured major surface 630 and a structured major surface 620. The non-structured surface 630 contacts a backing 600, and the surface 620 contacts a second structured adhesive layer 680 at its non-structured major surface 675. The structured major surface 670 of the adhesive layer 680 includes a plurality of reservoirs 641, while another plurality of reservoirs 640 reside between first adhesive layer 610 and the second adhesive layer 680.

One or more additional structured and/or substantially non-structured adhesive and/or non-adhesive layers can be interposed between the cap layer and the first adhesive layer of the multi-layer constructions described above or between any two layers of the multi-layer constructions. Each additional layer can be structured on one or both sides and can include one or more types of structures and adhesive and non-adhesive materials.

The laminate articles of the present invention can further include an optional release liner (not shown), which protects the adhesive layers and contents included within the adhesive matrix and/or reservoirs or channels from damage and contamination. The liner should be capable of being placed in intimate contact with an adhesive surface and may be subsequently removed without damaging the adhesive layer. Suitable liners include conventional release liners comprising a known sheet material such as coated polyester, polyester web, polyethylene web, polystyrene web, or polymer-coated paper. The liner is typically a polymer-coated paper with a silicone release coating or a fluoropolymer coating containing perfluorinated groups, a polyethylene coated polyethylene terepthalate (PET) film with silicone release coatings, or a cast polyolefin film with a silicone release coating. Non-limiting examples of liners include materials from Minnesota Mining & Manufacturing Company (3M) of St. Paul, Minn., Rexam Corporation of Iowa City, Iowa, Daubert Coated Products of Westchester, Ill., P.S Substrates, Inc., Schoeller Technical Papers, Inc., AssiDoman Inncoat GmbH, and P. W. A. Kunstoff GmbH.

The liner is typically a polymer-coated paper with a silicone release coating, a polyethylene coated polyethylene terepthalate (PET) film with silicone release coatings, or a cast polyolefin film with a silicone release coating.

The structures in the adhesive layers may be made as described in U.S. Pat. No. 6,197,397 B1 (Sher et al.) and U.S. Pat. No. 6,123,890 (Mazurek et al.), which are incorporated herein by reference. The topography may be created in the adhesive layer by any known technique, preferably by a contacting technique such as casting, coating, or compressing. The topography of the tool used to create the pattern may be made using any known technique, such as, for example, chemical etching, mechanical etching, laser ablation, photolithography, stereolithography, micromachining, knurling, cutting, or scoring.

Figure 7:
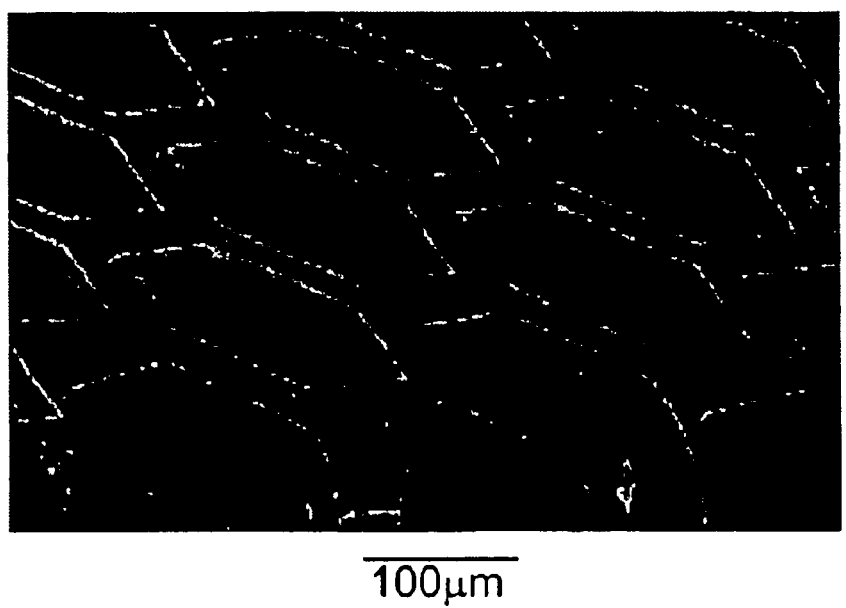
FIG. 7 is a scanning electron micrograph of a structured molding tool.

For example, the pattern of structures in the adhesive layer can be made by casting a layer of adhesive on a molding tool having a machined pattern. For example, FIG. 7 shows a scanning electron micrograph of the molding tool used to generate the structured topography in the adhesive layer of FIG. 2. The structured adhesive layer seen in FIG. 2 has a surface essentially replicating the inverse of the topography of the molding tool shown in FIG. 7.

Generally, the molding tool is pre-treated with a release coating prior to the embossing step. Once the tool is treated with the release coating, the adhesive can be extruded or solvent coated and dried onto the tool and laminated to a backing. The adhesive may be preheated to improve adhesion to the backing layer. In some applications, the adhesive is cured or cross-linked while on the tool to prevent premature cold flow. Alternatively, other adhesives are removed from the tool prior to curing. The exposed surface of the structured adhesive layer may be contacted with another adhesive layer to a form a second laminate or multi-layer construction. These lamination steps can be repeated to generate a multi-layer construction of the desired thickness. The adhesive layer(s) can then be cured or cross-linked with an energy source, such as heat, UV radiation, $e^-$ beam radiation, and the like. Depending on the type of adhesive, the adhesive may be solidified or physically cross-linked upon cooling the laminate to room temperature. After curing, cross-linking, or solidifying the adhesive, the structures on the surface of the adhesive layer substantially retain their shape over time. The selection of the adhesive plays a role in determining the long-term properties of the structured adhesive layer(s). The process can be scaled up as a continuous process utilizing the methods described in U.S. Pat. No. 6,123,890.

Additional membrane layers, transfer liners, release liners, adhesive layers (structured and non-structured), polymer films (structured and non-structured), and the like, can be laminated to the adhesive construction using lamination techniques that are well known to those skilled in the art.

Lamination of the cap layer to the structured surface of the adhesive and/or lamination of multiple structured layers creates a plurality of encapsulated reservoirs or channels within the adhesive coated article. The amount of void volume contained in the encapsulated reservoirs or channels can be tailored based on the adhesive composition and size and shape of the tooling used to generate the structures of each layer.

A variety of methods can be used to load medicinal ingredients into the laminates of the present invention. The choice of loading method will be determined by a number of factors including adhesive and/or solvent compatibility with the formulation (e.g., the medicinal ingredient itself, excipients, penetration enhancers, stabilizers, or other additives), desired final concentration of the medicinal ingredient in the adhesive, desired duration of administration, desired geometry of the system, preferred skin adhesion over the wearing time of the device, and desired release rate profile of the medicinal ingredient from the transdermal delivery system. Generally, the drug is loaded into the device in the absence of a release liner. By way of example, several loading methods are described below.

Methods for filling the reservoirs in the constructions of the invention include dipping, spraying, coating, sonicating, or powdering a prelaminate construction 905 with liquid or solid. Subsequent lamination of the prelaminate construction to a cap layer encapsulates the material within the reservoirs of the construction. Fluid filling of constructions in which a cap layer has already been applied to the structured surface, such as depicted in FIG. 1, can be accomplished by several means. Application of a pressure gradient can be used to load a fluid (such as a liquid containing a desired deliverable or non-deliverable substance) into the channels while displacing the air. This may be accomplished by simple mechanical means using, for example, a syringe/plunger. A particularly advantageous method of applying such a pressure gradient to fill the channels is by application of centrifugal force. If desired, venting may be supplied at the down stream (low pressure) ends of the channels such that air is displaced out of the channels as the fluid is introduced at the high pressure end. Conversely, centrifugal loading may be utilized in the absence of venting, such that the air is displaced countercurrent to the liquid being inserted. In this case the expelled air may be vented out through the same entry port via which the loading fluid is introduced.

Another means of filling channels with liquids in configurations including encapsulated reservoirs is through use of vacuum. Air may be evacuated from the channels until a sufficiently low pressure is reached, after which a liquid at a higher pressure (typically atmospheric) is brought into communication with the channels. Under this pressure differential, the liquid then fills the channels. This approach is especially suitable in cases in which venting is absent; that is, in which the only opening into the device is through the filling (liquid entry) port.

A pre-polymerization loading method can be used to incorporate medicinal ingredients into the pressure sensitive adhesive. This method involves directly solubilizing or dispersing the medicinal ingredient in the pressure sensitive adhesive composition. A transdermal delivery device can be prepared with the adhesive containing the medicinal ingredient using the methods described above. After curing, the medicinal ingredient may be dissolved in the adhesive matrix or dispersed within the interstitial spaces of the cross-linked polymer, depending on drug-adhesive compatibility.

Alternatively, post-polymerization loading can be used to incorporate one or more medicinal ingredients into a pre-formed (i.e., cured) pressure sensitive adhesive matrix. For example, a pre-formed pressure sensitive adhesive matrix may include a backing and one or more structured pressure sensitive adhesive layers. Post-polymerization loading involves introducing the pre-formed adhesive matrix into a solution of medicinal ingredient(s) in a solvent. The solvent can act (1) as a swelling agent for the adhesive, and/or (2) to load the medicinal ingredient into the exposed reservoirs and/or surface of the polymeric matrix.

A solvent of choice for these two post-polymerization loading techniques should maximize solubility of the medicinal ingredient without compromising the physical integrity of the pre-formed pressure sensitive adhesive matrix. Choice of solvent is based on the hydrophobicity or hydrophilicity of the medicinal ingredient and the composition of the various layers of the device. Suitable solvents include water, methanol, ethanol, acetonitrile, isopropanol, and buffers.

In the case of using a solvent as a swelling agent, the solvent containing the medicinal ingredient will be absorbed into the pressure sensitive adhesive during the swelling process. Generally, a sufficient quantity of solution is used to saturate the adhesive matrix and at least partially fill the reservoirs within each layer. Once a steady state or a desired concentration level is achieved, the matrix is then removed from the solution and allowed to dry by evaporating the solvent. This loading technique is limited by the solubility of the medicinal ingredient in the solvent, as well as the compatibility between the solvent and the adhesive.

In the case of using a solvent to load a medicinal ingredient into the exposed reservoirs and/or the adhesive matrix, the solvent containing the medicinal ingredient(s) can be loaded into the device either by applying a predetermined volume of solution onto the surface of the adhesive matrix or by soaking the adhesive matrix in a solution containing the medicinal ingredient. Diffusion of the solution into the interior of the device can be facilitated using, for example, agitation or gentle sonication. This loading technique requires the solvent to be incompatible with the adhesive matrix so that the loading is limited to the polymer surface. Alternatively, the amount loaded can be limited by contacting the adhesive matrix with the solution containing the medicinal ingredient for a predetermined time period.

The transdermal delivery devices of the invention can be a tape, a patch, a sheet, a dressing or any other form known to those skilled in the art. Generally, the device will be in the form of a patch of a size suitable to deliver a preselected amount of drug through the skin. Generally, the device will have a surface area of about 5 $cm^2$ to about 100 $cm^2$ and preferably about 10 $cm^2$ to about 40 $cm^2$.

A transdermal drug delivery device in accordance with this invention containing one or more medicinal ingredients can be used to treat any condition capable of treatment with the medicinal ingredient. The device can be placed on the skin and allowed to remain for a time sufficient to achieve or maintain the intended therapeutic effect. The time that constitutes a sufficient time can be selected by those skilled in the art with consideration of the flux rate of the device of the invention and upon the condition being treated.

Preparation of Adhesive Compositions

Adhesive A

A hydrophobic, thermoplastic pressure sensitive adhesive consisting of 90 parts by weight isooctyl acrylate and 10 parts by weight acrylic acid was prepared as described in U.S. Pat. No. 5,986,011, U.S. Pat. No. 5,637,646, and U.S. Pat. No. 5,753,768.

Adhesive B

A hydrophilic pressure sensitive adhesive was prepared by a two-step process. Step 1 involved forming a translucent, thermodynamically stable microemulsion of hydrophobic and hydrophilic monomers, held together by a surfactant, and step 2 involved initiating polymerization by application of UV-radiation. In an alternative method, the microemulsion of both hydrophobic and hydrophilic phases along with surfactant was pre-cured by using $\frac{1}{10}$ of the photoinitiator amount needed for a complete polymerization reaction. The pre-cured viscous solution was treated with UV radiation, resulting in web formation. The microemulsion pressure sensitive adhesive consisted of equal amounts of isooctyl acrylate, acrylic acid, and ethylene-10-monoacrylate. Other components in the formulation included propylene glycol, water, and BRIJ 97

(polyoxyethylene-10-oleyl ether), which was obtained from Aldrich Company (Milwaukee, Wis.).

EXAMPLES

Preparation of Component A

Structured adhesive layers were fabricated by embossing adhesive between a tool and a backing as described in copending application U.S. Ser. No. 09/974,710. The structured tool was cut from polyimide into a close-packed hexagonal pattern using laser ablation. Hexagonal posts were cut to be 125 microns tall and 115 microns wide at the top and 135 microns wide at the base. The repeat distance of the pattern was 175 microns. These dimensions created channels between the hexagonal posts that were 20 to 60 microns wide from bottom to top. The molding tool was treated with a release coating prior to the embossing step by coating a dilute solution of silicone over the tool. Once the tool was prepared, adhesive was extruded or coated onto the tool and laminated to a poly(ethylene terephthalate) backing. The adhesive was cured either while on the tool or removed from the tool prior to curing. The adhesive was cured under two UV lamps (General Electric Blacklight, 15W F15 T8.BL, Schenectady, N.Y.) using an energy dosage of 1500–1600 mJ/cm$^2$ for 5–20 minutes.

Once the adhesive was removed from the tool and cured, it was characterized to determine the degree of replication. Using the tool mentioned above, the structured adhesive assumed the shape of close-packed hexagonal reservoirs with 25 to 60 microns wide interconnected adhesive sidewalls. The height of the microstructured adhesive walls was determined by interferometry microscopy using a WYKO RST surface profiler (WYKO Corp., Tucson, Ariz.). The height of the walls typically was 70±5 microns. The samples were pressed against a glass substrate using a 4 lb (1.8 kg) roller, and the degree of wet-out was determined using a light microscope. The hexagonal pattern contacted the glass in only 40% of the area, leaving 60% of the well space void, since the glass contacted the adhesive only at the top edges of the reservoirs.

Example 1

Four multi-layer adhesive constructions (depicted in FIG. 8) were prepared using Adhesive A for Component A. Either a hydrophobic Adhesive A or hydrophilic Adhesive B layer was laminated to Component A to form a skin contact pressure sensitive adhesive layer.

Samples A-2 to A-4 included a structured hydrophobic adhesive layer filled with tetracycline (Sigma, St. Louis, Mo.), and the structured adhesive layer was covered by a cap layer.

Comparative Sample A-1 utilized a structured hydrophobic adhesive layer filled with tetracycline, but the structured layer was not covered by a cap layer. Comparative Sample A-5 utilized a non-structured adhesive layer covered with a layer of tetracycline. The tetracycline layer was not overlain with a cap layer.

Figure 8A:
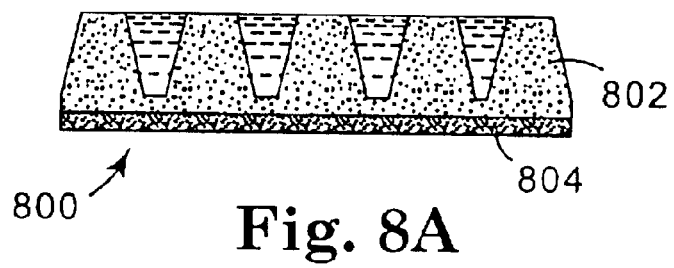
FIGS. 8A–8E show cross-sectional views of several transdermal delivery devices of Example 1.

Referring to FIG. 8A, the device 800 referred to as Sample A-1 included a structured adhesive layer 802 with reservoirs filled with tetracycline. The structured layer 802 was laminated to a hydrophobic adhesive skin contact pressure sensitive adhesive layer 804, and included no cap layer.

Figure 8B:
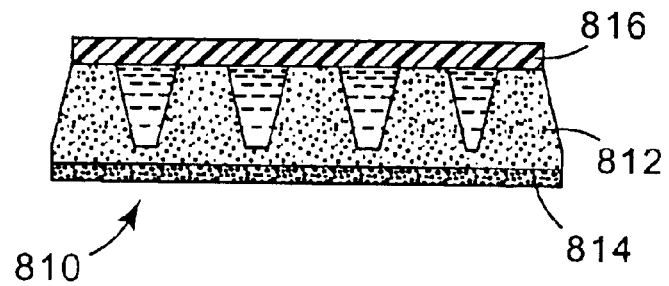

Referring to FIG. 8B, the device 810 referred to as Sample A-2 included a structured adhesive layer 812 with reservoirs filled with tetracycline. The structured layer 812 was laminated to a hydrophobic adhesive skin contact pressure sensitive adhesive layer 814 and capped with a non-structured hydrophobic adhesive layer 816.

Figure 8C:
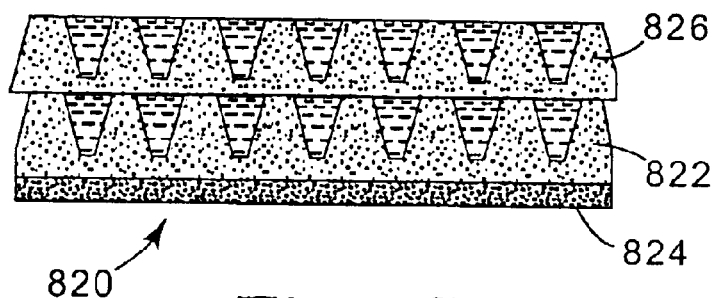

Referring to FIG. 8C, the device 820 referred to as Sample A-3 included a structured adhesive layer 822 with reservoirs filled with tetracycline. The structured layer 822 was laminated to a hydrophobic adhesive skin contact pressure sensitive adhesive layer 824 and was capped with a structured hydrophobic adhesive layer 826.

Figure 8D:
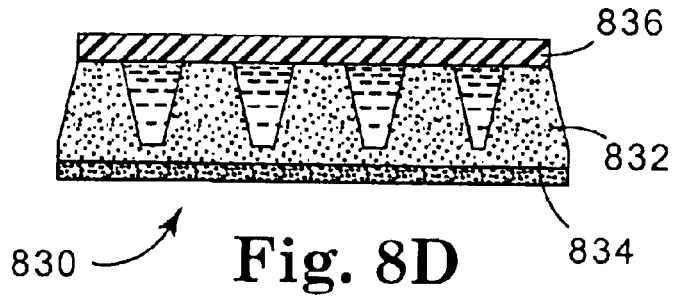

Referring to FIG. 8D, the device 830 referred to as Sample A-4 included a structured adhesive layer 832 with reservoirs filled with tetracycline. The structured layer 832 was laminated to a hydrophobic adhesive skin contact pressure sensitive adhesive layer 834 and was capped with a non-structured hydrophilic adhesive layer 836.

Figure 8E:
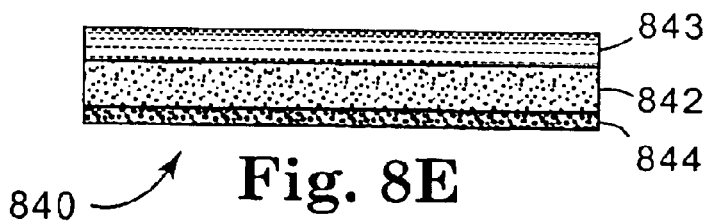

Referring to FIG. 8E, the device 840 referred to as Sample A-5 included a non-structured hydrophobic adhesive layer 842 covered with a layer 843 of tetracycline. The adhesive layer 842 was laminated to a hydrophobic adhesive skin contact pressure sensitive adhesive layer 844.

In vitro drug release studies were carried out by cutting 5 cm$^2$ patches from the drug loaded adhesive constructions. Each adhesive patch was placed between a glass slide and a plastic slide having an opening of 2 cm in diameter with the backing material facing the glass slide. The two slides were clamped together allowing only 3.14 cm$^2$ of adhesive area to be in contact with the release medium. The whole unit is placed in a drug release apparatus (Hanson SR8-Plus Dissolution Test System, Hanson Research Co., Chatsworth, Calif.) equipped with a paddle and a temperature control system. The matrix was brought into contact with 150 mL of the release medium (phosphate-buffered saline (pH 7.4) at 37° C. One-milliliter samples were taken at specified time periods up to 120 hrs. Each sample was placed into a tube or vial that was sealed and stored in the refrigerator until assayed. During the sampling period, the total volume of release medium was continuously measured to estimate the volume changes over time due to sampling and evaporation. The samples were filtered through 0.45 um Costar Nylon syringe filter to exclude any particulate and placed in 2 ml glass vials prior to HPLC (Waters 625 LC, Millipore Corporation, Milford, Mass.) and/or UV-Vis spectrometric analysis (SpectraMax Plus, Molecular devices Co, Sunnyvale, Calif.). The detection of tetracycline was at a dual UV wavelength of 375 nm and 405 nm. The drug concentration was determined by comparing a standard curve of tetracycline hydrate.

Figure 9:
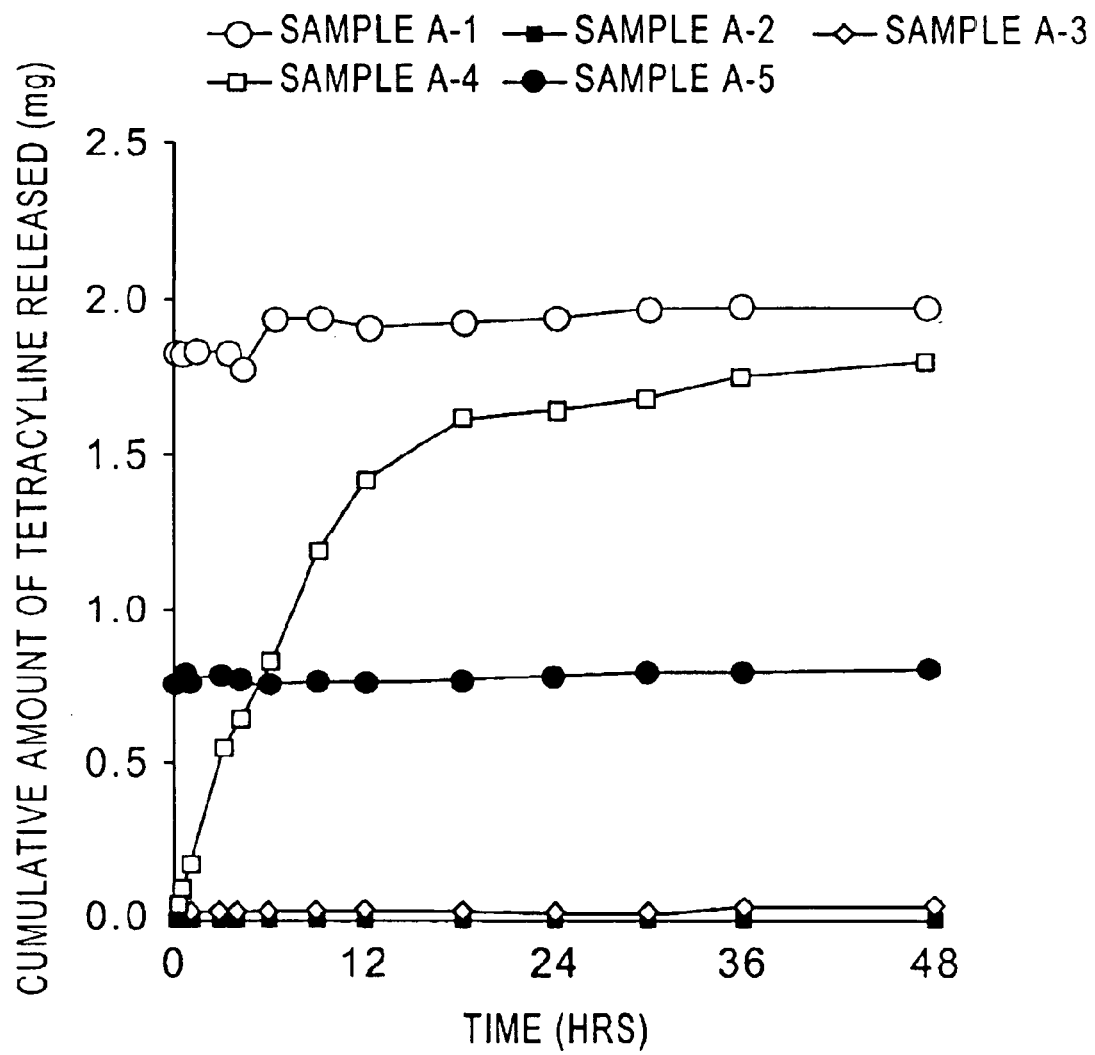
FIG. 9 shows a graph of drug release profiles of tetracycline from five different transdermal release constructions of FIG. 8.

Results of the in vitro drug release testing are shown in FIG. 9. Samples A-1 and A-5 (comparative samples) release drug immediately after contact with the phosphate buffer. Samples A-2, A-3, and A-4 show controlled release of tetracycline.

A number of embodiments of the invention have been described. Nevertheless, it will be understood that various modifications may be made without departing from the spirit and scope of the invention. Accordingly, other embodiments are within the scope of the following claims.

What is claimed is:

1. A transdermal delivery device comprising at least one pressure sensitive adhesive layer having a first major surface and a second major surface, wherein at least one of the first and second major surfaces is a structured surface; a cap layer in contact with a structured surface of the adhesive layer; and, at least one medicinal ingredient between the adhesive layer and the cap layer; wherein the cap layer in placed in intimate contact with the pressure senstive adhesive and cannot be removed without damage to the adhesive layer.

2. The device of claim 1, wherein the structured surface of the adhesive layer comprises a plurality of discrete reservoirs, the medicinal ingredient is in the reservoirs, and each reservoir has a void volume of less than about 100 μl.

3. The device of claim 1, wherein the cap layer is selected from a backing, a membrane, and adhesive layer.

4. The device of claim 1, wherein the medicinal ingredient is one of a gel, a paste, a foam, a powder, agglomerated particles, microencapsulated liquids, suspensions, liquids, and combinations thereof.

5. The device of claim 1, wherein the at least one medicinal ingredient comprises, antimicrobial agents, antifungal agents, cosmetic agents, or pharmaceutically effective excipients, and combinations thereof.

6. The device of claim 1, wherein the medicinal ingredient comprises a drug.

7. The device of claim 6, wherein the drug is selected from the group consisting of estradiol, testosterone, fentanyl, clonidine, nicotine, or nitroglycerin.

8. The device of claim 1, further comprising a skin contact pressure sensitive adhesive layer on the adhesive layer on a major surface opposite the cap layer.

9. The device of claim 8, wherein said cap layer comprises a backing.

10. The device of claim 1, wherein the cap layer comprises a skin contact pressure sensitive adhesive layer, said transdermal delivery device further comprising a backing on the adhesive layer on a major surface opposite the cap layer.

11. The transdermal delivery device according to claim 2, wherein at least one reservoir comprises a liquid selected from the group consisting of liquid drugs, drugs dissolved or dispersed in a liquid, skin penetration enhancers, and suitable combinations thereof.

12. The device of claim 8, further comprising a membrane layer between the adhesive layer and the skin contact pressure sensitive adhesive layer.

13. A method of administering a drug, comprising:
  a) providing a transdermal delivery device comprising: at least one pressure sensitive adhesive layer having a first major surface and a second major surface, wherein at least one of the first and second major surfaces is a structured surface, and a cap layer in contact with a structured surface of the adhesive layer, and at least one medicinal ingredient between the adhesive layer and the cap layer;
  b) placing the transdermal delivery device upon a patient's skin at an administration site; and
  c) maintaining contact with the skin for a time to deliver a therapeutically effective amount of the deliverable/therapeutic composition.

14. A transdermal delivery device, comprising:
  (a) a first adhesive layer having a first major surface and a second major surface, wherein at least one of the first and second major surfaces is a structured surface, wherein the first adhesive layer comprises at least one first array of reservoirs, and wherein the first array of reservoirs is at least partially filled with one of air and a first medicinal ingredient; and
  (b) a second adhesive layer having a first major surface and a second major surface, wherein at least one of the first and second major surfaces is a structured surface, wherein the second adhesive layer comprises at least one second array of reservoirs, and wherein the second array of reservoirs is at least partially filled with a second medicinal ingredient.

15. The device of claim 14, wherein the first major surface of the first adhesive layer is a structured surface, and the second major surface of the first adhesive layer is a non-structured surface, and wherein the first major surface of the first adhesive layer contacts a cap layer.

16. The device of claim 15, wherein the first major surface of the second adhesive layer is a non-structured surface, and the second major surface of the second adhesive layer is a structured surface, and wherein the first major surface of the second adhesive layer contacts the second major surface of the first adhesive layer.

17. The device of claim 14, wherein the first major surface of the first adhesive layer is a non-structured surface, and the second major surface of the first adhesive layer is a structured surface, and wherein the first major surface of the first adhesive layer contacts a cap layer.

18. The device of claim 17, wherein the first major surface of the second adhesive layer is a non-structured surface, and the second major surface of the second adhesive layer is a structured surface, and wherein the first major surface of the second adhesive layer contacts the second major surface of the first adhesive layer.

* * * * *

UNITED STATES PATENT AND TRADEMARK OFFICE
CERTIFICATE OF CORRECTION

PATENT NO. : 6,893,655 B2
DATED : May 17, 2005
INVENTOR(S) : Flanigan et al.

It is certified that error appears in the above-identified patent and that said Letters Patent is hereby corrected as shown below:

Column 4,
Line 36, delete "100" and insert in place therefor -- 110 --;

Column 6,
Line 12, delete "C8-C$_{36}$" and insert in place therefor -- C$_8$-C$_{36}$ --;
Line 30, delete "bomeol" and insert in place therefor -- borneol --;

Column 8,
Line 24, after "80 $\mu$L" insert -- ; --;

Column 16,
Line 58, after "layer" delete "in" and insert -- is --.

Signed and Sealed this

Fourth Day of October, 2005

JON W. DUDAS
*Director of the United States Patent and Trademark Office*